(12) United States Patent
Bando et al.

(10) Patent No.: US 9,427,434 B2
(45) Date of Patent: Aug. 30, 2016

(54) COATED PREPARATION

(75) Inventors: Hiroto Bando, Vernon Hills, IL (US); Yoshihiro Omachi, Osaka (JP); Kenichiro Kiyoshima, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1038 days.

(21) Appl. No.: 12/452,587

(22) PCT Filed: Jul. 10, 2008

(86) PCT No.: PCT/JP2008/062523
§ 371 (c)(1),
(2), (4) Date: Jan. 11, 2010

(87) PCT Pub. No.: WO2009/008487
PCT Pub. Date: Jan. 15, 2009

(65) Prior Publication Data
US 2010/0166853 A1  Jul. 1, 2010

(30) Foreign Application Priority Data

Jul. 12, 2007 (JP) ................................ 2007-183749

(51) Int. Cl.
| | |
|---|---|
| *A61K 31/4439* | (2006.01) |
| *A61K 9/16* | (2006.01) |
| *A61K 9/50* | (2006.01) |
| *A61K 9/20* | (2006.01) |

(52) U.S. Cl.
CPC ............ *A61K 31/4439* (2013.01); *A61K 9/1676* (2013.01); *A61K 9/2095* (2013.01); *A61K 9/5078* (2013.01)

(58) Field of Classification Search
USPC ......................................................... 424/400
See application file for complete search history.

(56) References Cited

U.S. PATENT DOCUMENTS

| | | | |
|---|---|---|---|
| 5,516,531 A | 5/1996 | Makino et al. | |
| 5,952,509 A | 9/1999 | Saito et al. | |
| 6,100,403 A | 8/2000 | Saito et al. | |
| 7,510,728 B2 | 3/2009 | Koike | |
| 7,976,853 B2* | 7/2011 | Ohkouchi et al. | ............ 424/400 |
| 2001/0056177 A1* | 12/2001 | Becker et al. | ................. 530/300 |
| 2004/0033258 A1 | 2/2004 | Koike | |
| 2004/0137052 A1 | 7/2004 | Uchiyama et al. | |
| 2004/0185105 A1* | 9/2004 | Berner et al. | ................. 424/486 |
| 2005/0074494 A1* | 4/2005 | Cheng et al. | .................. 424/471 |
| 2005/0095293 A1* | 5/2005 | Brauns et al. | ................. 424/469 |
| 2006/0089387 A1* | 4/2006 | Huang | ........................... 514/340 |

FOREIGN PATENT DOCUMENTS

| | | |
|---|---|---|
| EP | 1 552 832 A1 | 7/2005 |
| EP | 1 588 708 A1 | 10/2005 |
| JP | 05-262767 A | 10/1993 |
| JP | 2002-179558 A | 6/2002 |
| WO | WO 87/06130 A1 | 10/1987 |
| WO | WO 93/09781 A1 | 5/1993 |
| WO | WO 03/055525 A1 | 7/2003 |
| WO | WO 03/074032 A1 | 9/2003 |
| WO | WO 2004/006921 A1 | 1/2004 |
| WO | WO 2004/067001 A1 | 8/2004 |
| WO | WO 2004067001 A1 * | 8/2004 |
| WO | WO 2007126136 A2 * | 11/2007 |

OTHER PUBLICATIONS

Rowe, Handbook of Pharmaceutical Excipients—Citric Acid, 2003, Pharmaceutical Press, p. 158-160.*
University of Washington School of Pharmacy, Pharm 309 Pharmacey Calculations—Lesson 2 (p. 17), 2001, printed from http://courses.washington.edu/pharm309/calculations/, 3 pages.*
International Search Report in PCT/JP2008/062523, mailed Aug. 5, 2008, 2 pages.
Supplementary European Search Report dated Jun. 24, 2010, in corresponding EP 08791071.7, 6 pages.

* cited by examiner

*Primary Examiner* — Gigi Huang
(74) *Attorney, Agent, or Firm* — Foley & Lardner LLP

(57) ABSTRACT

The present invention provides a preparation containing pioglitazone or a salt thereof as an active ingredient, which shows high bioavailability of pioglitazone and less interindividual variation in blood drug concentration, as well as a preparation with suppressed color change during preservation. The preparation contains a core containing a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5, and a coating layer containing pioglitazone or a salt thereof. The coating layer may further contain mannitol or trehalose.

7 Claims, 2 Drawing Sheets

COATED PREPARATION

CROSS-REFERENCE TO RELATED APPLICATIONS

This application is a National Stage application of PCT/JP2008/062523, filed Jul. 10, 2008, which claims priority from Japanese application JP 2007-183749, filed Jul. 12, 2007.

TECHNICAL FIELD

The present invention relates to a preparation comprising pioglitazone or a salt thereof as an active ingredient, which has a core containing a particular organic acid to be mentioned below and a coating layer comprising pioglitazone or a salt thereof, and shows improved bioavailability of pioglitazone and a salt thereof.

BACKGROUND OF THE INVENTION

Patent Literature 1 discloses, in an attempt to improve the bioavailability of the active ingredient, a "pharmaceutical composition with a bioavailability of the active substance which is substantially independent of the gastric pH, for oral administration of active substances with pH-dependent solubilities and a dose number of more than 1 at a pH>5, comprising a plurality of pellets synthesized in each case from a) a core material, b) an optional insulating layer, c) an active substance layer and d) an optional coating, wherein the core material consists of one or more pharmaceutically acceptable organic acid(s) with a water solubility of more than 1 g/250 ml at 20° C., optionally with the addition of binders or other technological adjuvants."

However, the reference does not describe pioglitazone and a salt thereof.
Patent Literature 1: JP 2005-526738 A

DISCLOSURE OF THE INVENTION

Problems to be Solved by the Invention

The present inventors have studied pharmacokinetics of commercially available tablets containing pioglitazone hydrochloride (trade name: ACTOS® TABLETS), and found that a blood drug concentration after administration to a living organism shows interindividual variation. Hence, the present invention aims to provide a preparation comprising pioglitazone or a salt thereof as an active ingredient, which shows improved solubility of pioglitazone and less interindividual variation in blood drug concentration. In addition, the present invention also aims to provide a preparation showing suppressed color change during preservation.

Means of Solving the Problems

Generally, methods for improving the solubility of a drug include formation of a solid dispersion, atomization of drug, addition of a surfactant and the like. However, the solubility and absorption of pioglitazone and a salt thereof cannot be improved sufficiently by the general methods employed widely for improving solubility. The present inventors have further studied formulation of pioglitazone and a salt thereof, and found that superior effects of improving the solubility of pioglitazone, increasing the maximum drug concentration in blood and the area under the curve [AUC] of plasma concentration, and further, suppressing the interindividual variation in the drug concentration in blood can be afforded by producing a preparation containing a core comprising a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5, and a coating layer comprising pioglitazone or a salt thereof (particularly preferably, a preparation having a construct constituting the coating layer, which comprises a cellulose derivative as a skeleton and is maintained in an aqueous solvent, wherein pioglitazone or a salt thereof is dissolved in organic acid solution in the construct to afford an aqueous solution). Furthermore, the present inventors have found that the color change of the preparation (particularly color change under preservation conditions) can be suppressed by adding mannitol or trehalose to the coating layer of the preparation. The present inventors have further studied based on these findings and completed the present invention.

Accordingly, the present invention relates to
(1) a preparation comprising a core comprising a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5 (to be sometimes referred to simply as "organic acid" in the present specification), and a coating layer comprising pioglitazone or a salt thereof (to be sometimes referred to as "the coated preparation of the present invention" in the present specification);
(2) the preparation of the above-mentioned (1), wherein the pharmaceutically acceptable organic acid is at least one kind selected from citric acid, tartaric acid, malic acid and ascorbic acid;
(3) the preparation of the above-mentioned (1), wherein the pharmaceutically acceptable organic acid is citric acid;
(4) the preparation of the above-mentioned (1), wherein the coating layer comprises mannitol or trehalose;
(5) the preparation of the above-mentioned (1), wherein the pharmaceutically acceptable organic acid is citric acid crystal;
(6) the preparation of the above-mentioned (1), wherein the weight ratio of pioglitazone and the pharmaceutically acceptable organic acid is 1:4 to 1:26;
(7) the preparation of the above-mentioned (1), wherein the coating layer comprises cellulose or a cellulose derivative;
(8) the preparation of the above-mentioned (7), wherein the cellulose derivative is low-substituted hydroxypropylcellulose;
(9) the preparation of the above-mentioned (1), having a construct constituting the coating layer, which comprises a cellulose derivative as a skeleton and is maintained in an aqueous solvent;
(10) the preparation of the above-mentioned (9), wherein the construct is present for at least 10 min in McIlvaine buffer (pH 3.0, 900 mL) under the conditions of the Paddle Method (50 rpm);
(11) the preparation of the above-mentioned (1), wherein a construct constituting the coating layer, which comprises a cellulose derivative as a skeleton and is maintained in an aqueous solvent, wherein pioglitazone or a salt thereof is dissolved in an organic acid solution in the construct to afford an aqueous solution;
(12) the preparation of the above-mentioned (1), which shows bioavailability exceeding 75% in a dog; and the like.

Effect of the Invention

The coated preparation of the present invention can, as compared to conventional preparations containing pioglitazone or a salt thereof as an active ingredient, enhance bioavailability and suppress interindividual variation in absorption by promoting absorption of pioglitazone. To be precise, the coated preparation of the present invention can, as compared to conventional preparations, markedly increase the maximum blood concentration and AUC of pioglitazone after administration, and remarkably decrease the interindividual relative standard deviation (RSD) of AUC.

As mentioned above, the coated preparation of the present invention is a superior preparation, since it shows high bioavailability of pioglitazone, a sufficient effect with a low dose, and less interindividual variation in blood drug concentration.

In addition, the coated preparation of the present invention containing mannitol or trehalose in a coating layer is a superior preparation, since it shows high bioavailability of pioglitazone, less interindividual variation in blood drug concentration, and suppressed color change (particularly color change under preservation conditions).

BRIEF DESCRIPTION OF THE DRAWINGS

FIG. 1 shows the results of Experimental Example 7, wherein

FIG. 2 shows the results of Experimental Example 7, wherein

Figure 1A:
FIG. 1A is a photograph showing the state of granules before the dissolution test and FIG. 1B is a photograph showing the state of granules after the dissolution test.

The present invention is explained in detail in the following.

The coated preparation of the present invention comprises a core comprising a pharmaceutically acceptable organic acid with water solubility at 20° C. of not less than 10 mg/mL and $pK_{a1}$ negative common logarithm of the first acid dissociation constant $K_{a1}$) at 25° C. of not more than 5, and a coating layer comprising pioglitazone or a salt thereof.

The coated preparation of the present invention may be a single preparation having a core and a coating layer, or a collection of preparations each having a core and a coating layer. In addition, the coated preparation of the present invention may be a capsule produced by mixing a collection of preparations each having a core and a coating layer with additives as necessary and filling a capsule with the mixture. Furthermore, the coated preparation of the present invention may be a tablet produced by mixing a collection of preparations each having a core and a coating layer with additives as necessary and compression-molding the mixture, and the like.

The "core" of the coated preparation of the present invention may consist only of "a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5". Alternatively, it may consist of a composition of "a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5" and, for example, the below-mentioned additive and the like.

The "organic acid" contained in the "core" of the coated preparation of the present invention is "a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5". The water solubility at 20° C. is preferably not less than 50 mg/mL, more preferably not less than 100 mg/mL. The water solubility at 20° C. is preferably not more than 2000 mg/mL. $pK_{a1}$ (a negative common logarithm of the first acid dissociation constant $K_{a1}$) at 25° C. is preferably not more than 5, more preferably not more than 4. $pK_{a1}$ is preferably not less than 1. Preferred is "an organic acid with water solubility at 20° C. of not less than 300 mg/mL and $pK_{a1}$ (a negative common logarithm of the first acid dissociation constant $K_{a1}$) at 25° C. of not more than 4".

Specific examples of the "organic acid" include one or more kinds selected from citric acid, tartaric acid, malic acid and ascorbic acid, and the like. The "organic acid" may be any of hydrate and acidic salt. In addition, the "organic acid" is preferably in the form of a crystal, since the mechanical strength and chemical stability of the core containing the "organic acid" are not degraded during the production step of the preparation of the present invention, and in view of the acidity.

In the present specification, citric acid is a concept including citric acid monohydrate and anhydrous citric acid.

As the "organic acid", citric acid, tartaric acid and malic acid are preferable, and citric acid (particularly anhydrous citric acid) is more preferable from the aspects of actual performance as a pharmaceutical additive and the maximum amount of use for oral administration.

The average particle size of the "organic acid" is generally 100-1500 μm, preferably 300-1000 μm. The average particle size is measured, for example, using a laser diffraction particle distribution measurement apparatus (e.g., SYNPATEC HELOS-RODOS particle distribution measurement apparatus).

While the content of the "organic acid" in the "core" of the coated preparation of the present invention varies depending on the kind of the "organic acid" and the like, it is generally 20-95 parts by weight, preferably 40-80 parts by weight, per 100 parts by weight of the coated preparation.

While the average particle size of the "core" varies depending on the kind of the coated preparation of the present invention, it is generally 100-1500 μm, preferably 300-800 μm The "core" of the coated preparation of the present invention is covered with a coating layer comprising pioglitazone or a salt thereof.

With regard to "pioglitazone or a salt thereof" used for the coated preparation of the present invention, examples of the salt of pioglitazone include pharmacologically acceptable salts such as salts with inorganic acid, salts with organic acid, salts with acidic amino acid and the like.

Preferable examples of the salts with inorganic acid include salts with hydrochloric acid, hydrobromic acid, nitric acid, sulfuric acid, phosphoric acid and the like.

Preferable examples of the salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with acidic amino acid include salts with aspartic acid, glutamic acid and the like.

In addition, the pioglitazone may be any of anhydride or hydrates, and the pioglitazone may be further labeled with an isotope (e.g., $^3H$, $^{14}C$, $^{35}S$, $^{125}I$) and the like.

Pioglitazone or a salt thereof is preferably pioglitazone hydrochloride.

Pioglitazone and a salt thereof may be diluted with a diluent and the like that are generally used for medical field, food field and the like.

In the coated preparation of the present invention, the median size of pioglitazone and a salt thereof to be used as a starting material is preferably 0.5 to 50 μm. By adopting such median size, a coated preparation of pioglitazone or a salt thereof, which is superior in the dissolution property, can be obtained.

The above-mentioned preferable median size is applied to pioglitazone or a salt thereof used as the starting material [including a pulverized product obtained by pulverization during the process of producing an coated preparation, a mixed pulverized product obtained by pulverization together with an excipient (e.g., crystalline cellulose) and the like] for producing the coated preparation of the present invention. That is, the median size of pioglitazone or a salt thereof may change beyond the above range during a production process of the coated preparation of the present invention, or a preservation process of the coated preparation after production, by coagulation of pioglitazone or a salt thereof and the like. The pulverization is performed using a preparation forming machine such as a mortar, a jet mill, a hammer mill, a screen mill (P-3; Showa Kagaku Kikai Kosakusho Co., Ltd.) and the like.

In the present specification, the median size means a particle size that divides into crude particles and fine particles by 50% based on the weight distribution or number distribution. The median size can be measured, for example, by laser diffraction particle size distribution measurement apparatus (e.g., SYNPATEC HELOS-RODOS particle distribution measurement apparatus).

The dispersibility of pioglitazone or a salt thereof having the above-mentioned desired median size is preferably as defined by "particles of not more than 0.1 μm are contained at not more than 10% of the total amount, and particles of not less than 1000 μm are contained at not more than 10% of the total amount". The lower limit thereof is generally as defined by "particles of not more than 0.1 μm are contained at not less than 0.1% of the total amount, and particles of not less than 1000 μm are contained at not less than 0.1% of the total amount".

While the content of pioglitazone or a salt thereof in the coated preparation of the present invention varies depending on the dosage form, dose and the like of the coated preparation, it is generally 0.01-30 parts by weight, preferably 0.5-25 parts by weight, further preferably 0.5-20 parts by weight, per 100 parts by weight of the coated preparation.

In the coated preparation of the present invention, a weight ratio of pioglitazone and the aforementioned pharmaceutically acceptable organic acid is preferably 1:4-1:26, more preferably 1:4-1:20, more preferably 1:5-1:10. The weight of the "pioglitazone" means pioglitazone equivalent in a salt of pioglitazone.

In the coated preparation of the present invention, the amount of the "coating layer comprising pioglitazone or a salt thereof" to be used is generally 5-200 parts by weight, preferably 10-100 parts by weight, more preferably 20-90 parts by weight, per 100 parts by weight of the "core".

The coated preparation of the present invention preferably contains cellulose or a cellulose derivative in a coating layer. Of these, a cellulose derivative is preferable.

The cellulose derivative is a cellulose wherein a part of the cellulose molecule is substituted by other atom or functional group. Examples of the cellulose derivative include low-substituted hydroxypropylcellulose (L-HPC), hydroxypropylmethylcellulose, methylcellulose, hydroxypropylmethylcellulose phthalate, hydroxypropylmethylcellulose acetate succinate and the like. Of these, low-substituted hydroxypropylcellulose is preferable. More preferred is low-substituted hydroxypropylcellulose having a hydroxypropoxyl group content of 5-16 wt % (e.g., LH-11, LH-21, LH-31, LH-22, LH-32, LH-20, LH-30, LH-33 (trade name, manufactured by Shin-Etsu Chemical Co., Ltd.) etc.) and the like.

The content of the "cellulose or cellulose derivative" in the coating layer of the coated preparation of the present invention is generally 0.5-70 parts by weight, preferably about 2-about 50 parts by weight, more preferably about 2-about 30 parts by weight, per 100 parts by weight of the coating layer.

Since cellulose or a cellulose derivative (preferably cellulose derivative) is contained in the coating layer, the coated preparation of the present invention has a construct constituting a coating layer, which comprises cellulose or a cellulose derivative as a skeleton and is maintained in an aqueous solvent, wherein pioglitazone or a salt thereof is dissolved in an organic acid (solution) in the construct to afford an aqueous solution. As a result, the coated preparation of the present invention can, as compared to conventional preparations, remarkably increase the maximum blood concentration and AUC of pioglitazone after administration, and remarkably decrease interindividual relative standard deviation (RSD) in AUC.

In addition, since the coated preparation of the present invention has a construct constituting a coating layer, which comprises cellulose or a cellulose derivative as a skeleton and is maintained in an aqueous solvent, wherein pioglitazone or a salt thereof is dissolved in an organic acid (solution) in the construct to afford an aqueous solution, it can enhance bioavailability as compared to conventional preparations. Specifically, the bioavailability of the coated preparation of the present invention exceeds 75% when the preparation is administered to dogs.

In the present specification, the bioavailability can be determined by dividing AUC at the time of non-intravenous administration of a given amount of pioglitazone by AUC at the time of intravenous administration of the same amount of pioglitazone. For example, when the bioavailability of pioglitazone administered orally is to be calculated, the formula is the following:

$$\text{Bioavailability}(\%) = (\text{AUC of oral administration}/\text{AUC of intravenous administration}) \times 100$$

When pioglitazone is dissolved in the construct to afford an aqueous solution, a similar effect as achieved by the administration of solution can be provided, which is expected to increase maximum blood concentration, AUC and bioavailability.

Here, the aqueous solvent in the present specification includes water, KCl-HCl buffer (e.g., KCl-HCl buffer at pH 2.0), McIlvaine buffer (e.g., McIlvaine buffer at pH 2.2, pH 2.5 or pH 3.0) and the like. The "construct constituting a coating layer, which comprises a cellulose derivative as a skeleton and is maintained in an aqueous solvent" specifically means, for example, that the construct is present for not less than 10 minutes preferably in KCl-HCl buffer (pH 2.0, 900 mL) under conditions of Paddle Method (50 rpm), more preferably in McIlvaine buffer (pH 2.2, 900 ml) under conditions of Paddle Method (50 rpm), still more preferably in McIlvaine buffer (pH 2.5, 900 ml) under conditions of Paddle Method (50 rpm), particularly preferably in McIlvaine buffer (pH 3.0, 900 mL) under conditions of Paddle Method (50 rpm).

The Paddle Method in the present specification means measurement according to the Japanese Pharmacopoeia 14th Edition, General Tests, Dissolution Test Method 2, unless particularly indicated.

The coated preparation of the present invention may contain additives conventionally used in the technical field of formulation of preparations. Examples of the additive include excipient, disintegrant, binder, lubricant, colorant, pH regulator, surfactant, stabilizer, corrigent, sweetener, flavor, glidant, antistatic agent, light shielding agent, antioxidant, reducing agent, chelating agent and the like. These additives are used in an amount conventionally employed in the technical field of formulation of preparations. In addition, these additives may be used in a mixture of two or more kinds thereof in an appropriate ratio.

Examples of the excipient include saccharides; crystalline cellulose; starches such as corn starch, potato starch, wheat starch, rice starch, partly pregelatinized starch, pregelatinized starch, porous starch, dextrin, carboxymethyl starch and the like; anhydrous calcium phosphate, precipitated calcium carbonate, calcium silicate, powder cellulose, gelatin, light anhydrous silicic acid, synthetic aluminum silicate, magnesium aluminometasilicate, magnesium oxide, calcium phosphate, calcium carbonate, calcium sulfate.

Examples of the saccharides include sugar, starch sugar, lactose, honey and sugar alcohol. Two or more kinds of these saccharides may be used in a mixture in an appropriate ratio.

Examples of the sugar include sucrose, white soft sugar, glycosyl sucrose [coupling sugar (trade name)], fructooligosaccharide and palatinose.

Examples of the starch sugar include glucose, maltose, powdered starch syrup, starch syrup, fructose and trehalose.

Examples of the lactose include lactose, isomerized lactose (lactulose) and hydrogenated lactose (lactitol).

Examples of the honey include various kinds of honey generally used for eating.

Examples of the sugar alcohol include sorbitol, mannitol (specifically, D-mannitol), maltitol, hydrogenated glucose syrup, xylitol, reduced paratinose and erythritol.

The saccharides are preferably sugar alcohol, starch sugar and sucrose, more preferably mannitol, trehalose and sucrose. Of these, mannitol and trehalose are preferable. From the aspect of suppressing color change of the preparation (specifically color change under preservation conditions), in the coated preparation of the present invention, the "coating layer" is preferably to contain mannitol or trehalose.

When the saccharides are used for the coated preparation, the content thereof is for example, 5-90 parts by weight, preferably 5-40 parts by weight, per 100 parts by weight of the coated preparation.

Particularly, when the coated preparation of the present invention contains mannitol or trehalose, the content of "mannitol or trehalose" is preferably 5-40 parts by weight, more preferably 5-30 parts by weight, per 100 parts by weight of the coated preparation.

Examples of the crystalline cellulose include CEOLUS KG801, KG802, PH101, PH102, PH301, PH302, PH-F20, RC-A591NF (trade name, manufactured by Asahi Kasei Chemicals Corporation), including one called microcrystalline cellulose.

Examples of the disintegrant include carboxymethylcellulose, calcium carboxymethylcellulose (carmellose calcium), sodium carboxymethyl starch, carmellose sodium, croscarmellose sodium, crospovidone [preferably, Kollidon CL, CL-M, CL-F, CL-SF (trade name, BASF JAPAN LTD.); Polyplasdone XL, XL-10, INF-10 (trade name, ISP JAPAN LTD.)], low-substituted hydroxypropylcellulose [preferably low-substituted hydroxypropylcellulose having a hydroxypropoxyl group content of 5-16 wt %, such as LH-11, LH-21, LH-31, LH-22, LH-32, LH-20, LH-30, LH-33 (trade name, manufactured by Shin-Etsu Chemical Co., Ltd.) etc.], hydroxypropyl starch, cornstarch and partly pregelatinized starch.

When a disintegrant is used for the coated preparation of the present invention, the content of the disintegrant is, for example, 0.5-50 parts by weight, preferably 1-25 parts by weight, per 100 parts by weight of the coated preparation.

Examples of the binder include hydroxypropylcellulose [preferably HPC-SSL, SL, L (trade name, NIPPON SODA CO., LTD.)], hydroxypropylmethylcellulose, povidone (polyvinylpyrrolidone), arabic gum powder, sucrose, gelatin, pullulan, methylcellulose, crystalline cellulose, low-substituted hydroxypropylcellulose [preferably low-substituted hydroxypropylcellulose having a hydroxypropoxyl group content of 5-16 wt %, such as LH-11, LH-21, LH-31, LH-22, LH-32, LH-20, LH-30, LH-33 (trade name, manufactured by Shin-Etsu Chemical Co., Ltd.) etc.], macrogol, dextran, polyvinyl alcohol and starch paste. Of these, hydroxypropylcellulose is preferable.

When a binder is used for the coated preparation of the present invention, the content of the binder is, for example, 0.01-50 parts by weight, preferably 0.1-10 parts by weight, per 100 parts by weight of the coated preparation.

Examples of the lubricant include stearic acid, magnesium stearate, calcium stearate, talc, sucrose esters of fatty acids, sodium stearyl fumarate, waxes, DL-leucine, sodium lauryl sulfate, magnesium lauryl sulfate, macrogol and light anhydrous silicic acid (e.g., AEROSIL). Of these, magnesium stearate is preferable.

Examples of the colorant include foodcolors such as Food Yellow No. 5 (Sunset Yellow, same as Food yellow No. 6 in the US), Food Red No. 2, Food Blue No. 2 and the like, food lake colors, yellow ferric oxide (yellow iron oxide), diiron trioxide (red iron oxide), riboflavin, riboflavin organic acid ester (e.g., riboflavin butyrate), riboflavin phosphate or alkali metal salt thereof or alkaline earth metal salt thereof, phenolphthalein, titanium oxide, lycopene, beta-carotene.

Examples of the pH regulator include citrate, phosphate, carbonate, tartrate, fumarate, acetate and amino acid salt.

Examples of the surfactant include sodium lauryl sulfate, polysorbate 80, polyoxyethylene (160) polyoxypropylene (30) glycol, polyoxyethylene (196) polyoxypropylene (67) glycol and polyoxyethylene hydrogenated castor oil 60.

Examples of the stabilizer include sodium ascorbate, tocopherol, tetrasodium edetate, nicotinamide, cyclodextrins; alkaline earth metal salts (e.g., calcium carbonate, calcium hydroxide, magnesium carbonate, magnesium hydroxide, magnesium silicate, magnesium aluminate) and butylhydroxyanisole.

Examples of the corrigent include ascorbic acid, (anhydrous) citric acid, tartaric acid and malic acid.

Examples of the sweetener include aspartame, acesulfame potassium, thaumatin, saccharin sodium and dipotassium glycyrrhizinate. Of these, aspartame is preferable.

Examples of the flavor include menthol, peppermint oil, lemon oil and vanillin.

Examples of the glidant include light anhydrous silicic acid and hydrated silicon dioxide. Here, the light anhydrous silicic acid may be any containing hydrated silicon dioxide ($SiO_2 \cdot nH_2O$) (n is an integer) as a main component and, as concrete examples thereof, Sylysia 320 (trade name, FUJI SILYSIA CHEMICAL LTD.), AEROSIL 200 (trade name, NIPPON AEROSIL CO., LTD.) and the like can be used.

Examples of the antistatic agent include talc and light anhydrous silicic acid.

Examples of the light shielding agent include titanium oxide.

Examples of the antioxidant include dibutylhydroxytoluene (BHT), tocopherol, tocopherol ester (e.g., tocopherol acetate), ascorbic acid or alkali metal salt thereof or alkaline earth metal salt thereof, lycopene, beta-carotene.

Examples of the reducing agent include cystine and cysteine.

Examples of the chelating agent include EDTA or alkali metal salt thereof or alkaline earth metal salt thereof.

The coated preparation of the present invention may have an intermediate layer formed between the "core" and the "coating layer comprising pioglitazone or a salt thereof". Using such intermediate layer, an adverse effect (e.g., decomposition of pioglitazone) of the organic acid in the "core" on "pioglitazone or a salt thereof" in the "coating layer" can be prevented, and the durability of the coated preparation can be prolonged.

The dosage form of the coated preparation of the present invention is generally a solid preparation. Examples of the solid preparation include tablet, capsule, powder, granule and troche. Of these, granule, capsule and tablet are preferable.

The shape of the solid preparation is not particularly limited, and may be any of round, caplet, doughnut, oblong and the like.

The solid preparation may be coated with a coating agent, and may have a mark and letters for identification and further a score line for partition.

Examples of the coating base include sugar coating base, aqueous film coating base, enteric film coating base, sustained-release film coating base and the like.

As the sugar coating base, sucrose is used and one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trade name)], polyvinylpyrrolidone and the like; polysaccharides such as pullulan and the like; and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose, cellulose acetate and the like; acrylic acid polymers such as aminoalkyl methacrylate copolymer RS [Eudragit RS (trade name)], ethyl acrylate-methyl methacrylate copolymer suspension [Eudragit NE (trade name)] and the like; and the like.

Two or more kinds of the above-mentioned coating bases may be used in a mixture in an appropriate ratio. In addition, coating additives may also be used during coating.

Examples of the coating additive include light shielding agents and/or colorants such as titanium oxide, talc, ferric oxide and the like; plasticizers such as polyethylene glycol, triethyl citrate, castor oil, polysorbates and the like; and the like.

The coated preparation of the present invention can be produced by using the above-mentioned various additives according to a conventional method in the technical field of formulation of preparations.

For example, the coated preparation of the present invention can be produced by
(1) mixing an organic acid with additives where necessary to give a "core containing an organic acid",
(2) forming a "coating layer comprising pioglitazone or a salt thereof" on the surface of the core by coating the "core containing an organic acid" with pioglitazone or a salt thereof and additives where necessary, and
(3) drying and sieving the obtained coated product as necessary.

In addition, the coated preparation of the present invention can also be produced by mixing the coated product after drying and sieving with an additive as necessary, and compression molding or filling the mixture in a capsule.

Here, the mixing (including granulation, drying, milling and the like) is performed, for example, using a preparation forming machine such as a V-type mixer, a tumbler mixer, a high speed agitating granulator (FM-VG-10; POWREX CORPORATION), an all-round kneader (Hata Tekkosho, Co., Ltd.), a fluidized-bed dryer/granulator (LAB-1, FD-3S, FD-3SN; POWREX CORPORATION), a box vacuum dryer (Kusunoki Machinery Co., Ltd.), a screen mill (P-3; Showa Kagaku Kikai Kosakusho Co., Ltd.), centrifugal fluidized-bed granulator (CF-mini, CF-260, CF-360; Freund Corporation), dry granulator, spray drying granulator, rotating fluidized-bed granulator (MP10; POWREX CORPORATION) and the like.

For coating, for example, a preparation producing machine such as a centrifugal fluidized-bed granulator (CF-mini, CF-260, CF-360; Freund Corporation), a rolling granulator (MP10; POWREX CORPORATION), a general fluidized-bed coating apparatus, a wurster type coating apparatus and the like is used, and a centrifugal fluidized-bed granulator is preferably used.

The compression molding is performed, for example, by punching generally at a pressure of 0.3-35 kN/cm$^2$ using a single-punch tableting machine (KIKUSUI SEISAKUSHO LTD.), a rotary tableting machine (KIKUSUI SEISAKUSHO LTD.), Auto-graph (Shimadzu Corporation) and the like.

Examples of the capsule to be used for capsule filling include gelatin capsule, hydroxypropylmethylcellulose (HPMC) capsule, pullulan capsule and the like (preferably, hydroxypropylmethylcellulose (HPMC) capsule).

The above-mentioned "core containing organic acid" is coated by the following method or a method analogous thereto:
1) a method including spraying pioglitazone or a salt thereof together with additives as necessary (preferably, an excipient [preferably crystalline cellulose (which may be omitted), saccharides (preferably mannitol, trehalose, sucrose)], a disintegrant (preferably L-HPC)) onto the "core containing an organic acid, while spraying a solution of a binder (preferably, hydroxypropylcellulose) in a solvent [e.g., one or more kinds selected from water, alcohol (e.g., methanol, ethanol, propanol, isopropanol), acetone and acetonitrile; preferably water or isopropanol] (the solution may be a dispersion)";
2) a method including spraying a solution of a binder (preferably, hydroxypropylcellulose) containing pioglitazone or a salt thereof, and an additive as necessary (preferably, excipient [preferably crystalline cellulose (which may be omitted), saccharides (preferably, mannitol, trehalose, sucrose)], a disintegrant (preferably, L-HPC)) in a solvent

[e.g., one or more kinds selected from water, alcohol (e.g., methanol, ethanol, propanol, isopropanol), acetone, acetonitrile; preferably water or isopropanol] (the solution may be dispersion) onto the "core containing organic acid";

3) a method including spraying pioglitazone or a salt thereof together with an additive as necessary (preferably, excipient [preferably, crystalline cellulose (which may be omitted), saccharides (preferably, mannitol, trehalose, sucrose)], a disintegrant (preferably, L-HPC), and a binder (preferably, hydroxypropylcellulose)) onto the "core containing organic acid", while spraying a solvent [e.g., one or more kinds selected from water, alcohol (e.g., methanol, ethanol, propanol, isopropanol), acetone, acetonitrile; preferably water or isopropanol]; or 4) a method including spraying pioglitazone or a salt thereof together with cellulose or a cellulose derivative [preferably, cellulose derivative (more preferably L-HPC)], and an additive as necessary (preferably, excipient [preferably crystalline cellulose (which may be omitted), saccharides (preferably, mannitol, trehalose, sucrose)] onto the "core containing organic acid", while spraying a solution of a binder (preferably, hydroxypropylcellulose) in a solvent [e.g., one or more kinds selected from water, alcohol (e.g., methanol, ethanol, propanol, isopropanol), acetone and acetonitrile; preferably water or isopropanol] (the solution may be dispersion).

The "core" of the coated preparation of the present invention preferably consists of at least one kind of organic acid selected from citric acid, tartaric acid, malic acid and ascorbic acid [preferably citric acid (particularly anhydrous citric acid)].

In addition, the "coating layer comprising pioglitazone or a salt thereof" in the coated preparation of the present invention preferably consists of pioglitazone or a salt thereof (preferably pioglitazone hydrochloride), an excipient [preferably crystalline cellulose (which may be omitted), saccharides (preferably mannitol, trehalose, sucrose; more preferably mannitol)], a disintegrant (preferably L-HPC) and a binder (preferably hydroxypropylcellulose), or it is a coating layer consisting of pioglitazone or a salt thereof (preferably pioglitazone hydrochloride), an excipient [preferably crystalline cellulose (which may be omitted), saccharides (preferably mannitol, trehalose, sucrose; more preferably mannitol)], cellulose or a cellulose derivative (preferably a cellulose derivative, more preferably L-HPC) and a binder (preferably hydroxypropylcellulose).

A specific example of the coated preparation of the present invention is the following preparation (1).

Preparation (1):

A preparation comprising a coated particle consisting of a core, which contains a pharmaceutically acceptable organic acid with water solubility at 20° C. of not less than 10 mg/mL and $pK_{a1}$ (a negative common logarithm of the first acid dissociation constant $K_{a1}$) at 25° C. of not more than 5, and a coating layer containing pioglitazone or a salt thereof (one embodiment of the coated preparation of the present invention, hereinafter sometimes to be referred to as "the coated particle of the present invention").

The preparation (1) is exemplified by a) the coated particle itself of the present invention, b) a capsule produced by mixing the coated particle of the present invention with additives as necessary, and filling a capsule with the mixture, and an additive as necessary, c) a tablet produced by mixing the coated particle of the present invention with additives as necessary, and compression-molding the mixture and the like.

Regarding preparation (1), the "core" may be a "pharmaceutically acceptable organic acid with water solubility at 20° C. of not less than 10 mg/ml, and $pK_{a1}$ (a negative common logarithm of the first acid dissociation constant $K_{a1}$) at 25° C. of not more than 5" itself, or can also be produced by granulating the "organic acid", together with the aforementioned additives (e.g., excipient, binder) as necessary. Where necessary, operations such as drying, sieving and the like may be performed after granulation.

Preferred as the "organic acid" is citric acid (particularly, anhydrous citric acid).

The content of the "organic acid" in the "core" of the coated particle of the present invention is preferably 20-90 parts by weight, more preferably 40-80 parts by weight, per 100 parts by weight of the coated particle of the present invention.

In preparation (1), the average particle size of the "core" is preferably 100-1500 μm, more preferably 300 μm-800 μm.

The coated particle of the present invention can be produced by coating the "core" with the "coating layer comprising pioglitazone or a salt thereof".

The coated particle of the present invention includes not only a coated particle wherein the "core" is completely coated with the "coating layer comprising pioglitazone or a salt thereof" (100% of the total surface area of the core) but also a coated particle wherein the "core" is partially coated with the "coating layer comprising pioglitazone or a salt thereof" (e.g., 50% or more of the total surface area of the core).

The "coating layer" may contain the aforementioned additives as necessary. Preferable examples of the additives include excipients [e.g., crystalline cellulose, saccharides (e.g., mannitol, trehalose, sucrose)], disintegrants (e.g., L-HPC), binders (e.g., hydroxypropylcellulose) and the like. In addition, the additive is preferably an excipient [e.g., crystalline cellulose, saccharides (e.g., mannitol, trehalose, sucrose)], cellulose or a cellulose derivative (e.g., L-HPC), a binder (e.g., hydroxypropylcellulose) and the like.

The coated particle of the present invention preferably contains a core consisting of at least one kind of organic acid selected from citric acid, tartaric acid, malic acid and ascorbic acid [preferably citric acid (particularly anhydrous citric acid)], and a coating layer consisting of pioglitazone or a salt thereof (preferably pioglitazone hydrochloride), an excipient [preferably, crystalline cellulose (which may be omitted), saccharide (preferably, mannitol, trehalose, sucrose; more preferably, mannitol)], a disintegrant (preferably, L-HPC) and a binder (preferably, hydroxypropylcellulose). Alternatively, it is a coated particle comprising a core consisting of one or more kinds of organic acids selected from citric acid, tartaric acid, malic acid and ascorbic acid [preferably citric acid (particularly citric anhydride)], and a coating layer consisting of pioglitazone or a salt thereof (preferably pioglitazone hydrochloride), an excipient [preferably, crystalline cellulose (which may be omitted), saccharides (preferably, mannitol, trehalose, sucrose; more preferably mannitol)], cellulose or a cellulose derivative (e.g., L-HPC) and a binder (preferably, hydroxypropylcellulose).

When a tablet is produced using the coated particle of the present invention, the coated particle is preferably further coated with a disintegrant.

To be specific, the coated particle of the present invention produced by the above-mentioned method is coated with a disintegrant, together with an additive (preferably a binder) where necessary.

Preferred as the disintegrant are carmellose calcium, croscarmellose sodium, crospovidone and the like.

Preferred as the binder are hydroxypropylcellulose [e.g., HPC-SL, HPC-L (trade name)] and the like.

To be specific, "the coated particles of the present invention" is coated with a disintegrant according to the following method or a method analogous thereto.

1) a method including spraying a disintegrant with an additive (e.g., excipient) as necessary, while spraying a solution of a binder in a solvent [e.g., one or more kinds selected from water, alcohol (e.g., methanol, ethanol, propanol, isopropanol), acetone and acetonitrile; preferably water or isopropanol] (the solution may be a dispersion) on the coated particle of the present invention;
2) a method including spraying a binder solution containing a disintegrant, and an additive as necessary (e.g., excipient) in a solvent [e.g., one or more kinds selected from water, alcohol (e.g., methanol, ethanol, propanol, isopropanol), acetone, acetonitrile; preferably water or isopropanol] (the solution may be dispersion) on the coated particle of the present invention; or
3) a method including spraying a disintegrant and a binder together with an additive as necessary (e.g., excipient), while spraying a solvent [e.g., one or more kinds selected from water, alcohol (e.g., methanol, ethanol, propanol, isopropanol), acetone, acetonitrile; preferably water or isopropanol] on the coated particle of the present invention.

When the coated particle of the present invention is coated with a disintegrant, the amount of the "disintegrant" to be used is generally 0.1-100 parts by weight, preferably 0.5-50 parts by weight, more preferably 1-30 parts by weight, per 100 parts by weight of "the coated particle of the present invention".

The average particle size of the coated particle of the present invention is generally 200-5000 µm, preferably 200-3000 µm, more preferably 300-2000 µm, particularly preferably 350-1000 µm. The coated particle of the present invention is preferably a granule. Here, the granule preferably has the particle size defined in the Japanese Pharmacopoeia 14th Edition, i.e., in a particle size test of preparations, a particle size wherein "the whole amount passes through #10 (1700 µm) sieve, not more than 5% of the total amount remains on #12 (1400 µm) sieve, and not more than 15% of the total amount passes through #42 (355 µm) sieve".

When preparation (1) is a tablet or a capsule, the coated particle of the present invention (which may be coated with a disintegrant as mentioned above) is compression-molded with any additive or filled in a capsule with any additive.

Examples of the additive include lubricant (preferably magnesium stearate, talc), antistatic agent (preferably light anhydrous silicic acid) and the like.

The content of the coated particle of the present invention in preparation (1) is, for example, 10-99 parts by weight, preferably 30-99 parts by weight, per 100 parts by weight of preparation (1).

The coated preparation of the present invention can be safely administered orally to a mammal (e.g., mouse, rat, rabbit, cat, dog, bovine, horse, monkey, human).

While the dose of the coated preparation of the present invention varies depending on the subject of administration, severity of the disease and the like, it can be selected from the range affording the effective amount of pioglitazone or a salt thereof. Specifically, the dose is, for example, generally 7.5-60 mg/day, preferably 10-60 mg/day, further preferably 10-40 mg/day, as pioglitazone for one adult (body weight 60 kg), which may be administered in 2-3 portions a day.

The coated preparation of the present invention is useful, for example, as an agent for the prophylaxis or treatment of diseases such as diabetes (e.g., type-1 diabetes, type-2 diabetes, gestational diabetes), hyperlipidemia (e.g., hypertriglyceridemia, hypercholesterolemia, hypoHDL-cholesterolemia, postprandial hyperlipidemia), impaired glucose tolerance (IGT), diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder etc.], obesity, osteoporosis, cachexia (e.g., carcinocachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), insulin resistance syndrome, Syndrome X, dysmetabolic syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory disease [e.g., Alzheimer's disease, chronic rheumatoid arthritis, spondylitis deformans, osteoarthritis, lumbago, gout, postoperative or traumatic inflammation, regression of puffiness, neuralgia, pharyngolaryngitis, cystitis, hepatitis (inclusive of nonalcoholic steatohepatitis), pneumonia, pancreatitis, inflammatory colitis, ulcerative colitis], visceral obesity syndrome, arteriosclerosis (e.g., atherosclerosis), disseminated sclerosis, sepsis, psoriasis, Parkinson's disease, atopic dermatitis and the like; or secondary prevention (e.g., secondary prevention of cardiovascular event such as myocardial infarction and the like) and suppression of progression (e.g., suppression of progression from impaired glucose tolerance to diabetes, suppression of progression to arteriosclerosis in diabetes patients) of the above-mentioned various diseases.

The coated preparation of the present invention can be used in combination with an active ingredient other than pioglitazone and a salt thereof (hereinafter sometimes to be abbreviated as concomitant component). In this case, the timing of administration of pioglitazone or a salt thereof and that of the concomitant component are not limited, and they may be administered to an administration subject simultaneously or in a staggered manner. In addition, the coated preparation of the present invention and the concomitant component may be administered to an administration subject as two kinds of preparations each containing the active ingredient, or a single preparation containing the both active ingredients.

The dose of the concomitant component can be appropriately determined based on the dose employed clinically.

Use of the concomitant component in this way provides superior effects such as 1) enhancing the action of the coated preparation of the present invention or the concomitant component (synergistic effect on the action of the pharmaceutical agents), 2) reducing the dose of the coated preparation of the present invention or the concomitant component (effect of reducing the dose of pharmaceutical agents as compared to a single drug administration), 3) reducing the secondary action of the coated preparation of the present invention or the concomitant component, and the like.

Examples of the concomitant component include therapeutic drug for diabetes (excluding pioglitazone and a salt thereof), therapeutic drug for diabetic complications, therapeutic drug for hyperlipidemia, antihypertensive drug, antiobesity drug, diuretic drug, antithrombotic drug and the like.

These active ingredients may be low-molecular-weight compounds, or high-molecular-weight protein, polypeptide, antibody, vaccine and the like. In addition, two or more kinds of the active ingredients may be used in a mixture in an appropriate ratio.

Examples of the therapeutic drug for diabetes include insulin preparations (e.g., animal insulin preparations extracted from the pancreas of bovine, swine; human insulin preparations synthesized by genetic engineering using *Escherichia coli* or yeast; zinc insulin; protamine zinc insulin; fragment or derivative of insulin (e.g., INS-1)), α-glucosidase inhibitors (e.g., voglibose, acarbose, miglitol, emiglitate), biguanides [e.g., metformin, buformin or a salt thereof (e.g., hydrochloride, fumarate, succinate)], insulin sensitizer (excluding pioglitazone and a salt thereof) (e.g., rosiglitazone or a salt thereof (preferably maleate), Reglixane, Netoglitazone, Rivoglitazone, Tesaglitazar, Ragaglitazar, Muraglitazar, Edaglitazone, Naveglitazar, Metaglidasen, LY-510929, Balaglitazone, T-131 or a salt thereof, THR-0921), insulin secretagogues [e.g., sulfonylurea (e.g., tolbutamide, glibenclamide, gliclazide, chlorpropamide, tolazamide, acetohexamide, glyclopyramide, glimepiride, glipizide, glybuzole), non-sulfonylurea insulin secretagogues (e.g., repaglinide, nateglinide, mitiglinide or calcium salt hydrate thereof)], GLP-1 receptor agonists [e.g., GLP-1, GLP-1MR agent, NN-2211, exendin-4, BIM-51077, Aib(8,35)hGLP-1(7,37)NH$_2$, CJC-1131], dipeptidyl-peptidase IV inhibitors (e.g., vildagliptin, saxagliptin, NVP-DPP-278, PT-100, NVP-DPP-728, P32/98, P93/01, TS-021, sitagliptin, denagliptin, T-6666, alogliptin or a salt thereof (preferably benzoate), 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof (preferably succinate), 2-[2-(3-(R)-amino-piperidin-1-yl)-5-fluoro-6-oxo-6H-pyrimidin-1-ylmethyl]-benzonitrile or a salt thereof (preferably tartrate)), β3 agonists (e.g., AJ-9677), amylin agonists (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance-improving drug, somatostatin receptor agonists (e.g., compounds described in WO01/25228, WO03/42204, WO98/44921, WO98/45285, WO99/22735), glucokinase activators (e.g., Ro-28-1675), GPR40 agonist, GIP (glucose-dependent insulinotropic peptide) and the like.

Examples of the therapeutic drug for diabetic complications include aldose reductase inhibitors (e.g., tolrestat, epalrestat, zenarestat, zopolrestat, minalrestat, fidarestat, CT-112, ranirestat), neurotrophic factors (e.g., NGF, NT-3, BDNF), neurotrophic factor production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole)], PKC inhibitors (e.g., ruboxistaurin mesylate), AGE inhibitors (e.g., ALT946, pimagedine, pyratoxanthine, N-phenacylthiazolium bromide (ALT766), EXO-226, ALT-711, pyridorin, pyridoxamine), active oxygen scavengers (e.g., thioctic acid), cerebral vasodilators (e.g., tiapuride, mexiletine), somatostatin receptor agonists (e.g., BIM23190) and apoptosis signal regulating kinase-1 (ASK-1) inhibitors.

Examples of the therapeutic drug for hyperlipidemia include HMG-CoA reductase inhibitors (e.g., pravastatin, simvastatin, lovastatin, atorvastatin, fluvastatin, lipantil, itavastatin, rosuvastatin or a salt thereof (e.g., sodium salt, calcium salt)), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate), squalene synthase inhibitors (e.g., compounds described in WO97/10224, for example, 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzooxazepin-3-yl]acetyl]piperidine-4-acetic acid), ACAT inhibitors (e.g., avasimibe, eflucimibe, pactimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the antihypertensive drug include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, olmesartan medoxomil, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, nicardipine, amlodipine, efonidipine), potassium channel openers (e.g., levcromakalim, L-27152, AL0671, NIP-121), clonidine and the like.

Examples of the antiobesity drug include antiobesity drug acting on the central nervous system [e.g., dexfenfluramine, fenfluramine, phentermine, sibutramine, anfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist; 11β-hydroxysteroid dehydrogenase inhibitors (e.g., BVT-3498)], pancreatic lipase inhibitors (e.g., orlistat, cetilistat), β3 agonists (e.g., AJ-9677), anorectic peptides [e.g., leptin, CNTF (ciliary neurotrophic factor)], cholecystokinin agonists (e.g., lintitript, FPL-15849), feeding deterrents (e.g., P-57), ACC2 inhibitors (e.g., CP-640186) and the like.

Examples of the diuretic drug include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the antithrombotic drug include heparin (e.g., heparin sodium, heparin calcium, dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride and the like) and the like.

Of the above-mentioned concomitant components, biguanides (preferably metformin), insulin secretagogues (preferably sulfonylurea, non-sulfonylurea insulin secretagogues, more preferably glimepiride, nateglinide, mitiglinide or calcium salt hydrate thereof), α-glucosidase inhibitors (preferably voglibose) and the like are preferable. When using two or more kinds of concomitant components, the combination of biguanide (preferably metformin) and insulin secretagogue (preferably sulfonylurea, more preferably glimepiride) is preferable.

EXAMPLES

While the following Comparative Examples, Examples, Reference Examples and Experimental Examples explain the present invention in detail, they are not to be construed as limiting the present invention.

In the Comparative Examples, Examples and Reference Examples, as additives for pharmaceutical preparations (e.g., sucrose, crystalline cellulose, L-HPC (low-substituted hydroxypropylcellulose), hydroxypropylcellulose, mannitol, magnesium stearate, carmellose calcium, croscarmellose sodium, crospovidone, trehalose), products compatible with the Japanese Pharmacopoeia 14th Edition or Japanese Pharmaceutical Excipients 2003 compatible products were used.

Comparative Example 1

Pioglitazone hydrochloride (hereinafter to be abbreviated as "compound A", 66.12 g. 60 g as pioglitazone) and lactose (DMV international, 152.68 g) were thoroughly mixed. The obtained powder mixture was fed into a fluidized-bed granulator (Labo-1, POWREX CORPORATION), and granulated while spraying an aqueous solution (6 w/w %) of hydroxypropylcellulose (HPC-L, NIPPON SODA CO., LTD.). The obtained granules were mixed with carmellose calcium (GO-TOKU CHEMICAL COMPANY Ltd., 14.4 g) and magnesium stearate (TAIHEI CHEMICAL INDUSTRIAL CO., LTD., 0.8 g). The obtained powder mixture (180 g) and anhydrous citric acid crystal (Wako Pure Chemical Industries, Ltd., 360 g) were filled in No. 00 gelatin capsules (Capsugel) to give capsules having the following composition per capsule.

TABLE 1

| | |
|---|---|
| anhydrous citric acid crystal | 360.0 mg |
| compound A | 49.6 mg |
| lactose | 114.5 mg |
| hydroxypropylcellulose | 4.5 mg |
| carmellose calcium | 10.8 mg |
| magnesium stearate | 0.6 mg |
| total | 540.0 mg |

Comparative Example 2

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Nonpareil-101 (Freund Corporation, 150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules in the range of 16-30 mesh (aperture 0.50-1.00 mm). The granules (450 mg) were filled in No. 0 gelatin capsules (Capsugel) to give capsules having the following composition per capsule.

TABLE 2

| | |
|---|---|
| Nonpareil-101 | 300.0 mg |
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Comparative Example 3

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Fumaric acid crystal (Wako Pure Chemical Industries, Ltd.) was sieved with a round sieve to give a fumaric acid crystal on 30 mesh (aperture 0.50 mm) or above. Fumaric acid crystal (150 g) was fed into a centrifugal fluidized-bed granulator (CF-mini, Freund Corporation), and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and passed through a round sieve to give granules of 16-30 mesh (aperture 0.50-1.00 mm). The granules (450 mg) were filled in No. 0 gelatin capsules (Capsugel) to give capsules having the following composition per capsule.

TABLE 3

| | |
|---|---|
| fumaric acid crystal | 300.0 mg |
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Comparative Example 4

Hydroxypropylcellulose (HPC-L, NIPPON SODA CO., LTD., 6.0 g) was added to purified water (93.0 g), mixed, and dissolved. To this aqueous solution were added talc (Matsumurasangyo Co., Ltd., 12.5 g) and compound A (24.8 g), and mixed to give a suspension. Anhydrous citric acid crystal (Jungbunzlauer, 150 g) was fed into a fluidized-bed granulator (Lab-1, POWREX CORPORATION), and coated with the above-mentioned suspension (136.3 g) to give granules having the following composition per 386.6 mg.

TABLE 4

| | |
|---|---|
| anhydrous citric acid crystal | 300 mg |
| compound A | 49.6 mg |
| talc | 25 mg |
| hydroxypropylcellulose | 12 mg |
| total | 386.6 mg |

Comparative Example 5

Compound A (24.8 g) and mannitol (ROQUETTE, 197 g) were thoroughly mixed to give a dusting powder. Anhydrous citric acid crystal (Jungbunzlauer, 150 g) was fed into a centrifugal fluidized-bed granulator (CF-mini, Freund Corporation), and coated with the above-mentioned dusting powder while spraying an aqueous solution (3 w/v %) of hydroxypropylcellulose (HPC-SL, NIPPON SODA CO., LTD.). The obtained spherical granules were dried under reduced pressure at 40° C. for 16 hr, and sieved with a round sieve to give granules at the range of 12-30 mesh (aperture 0.50-1.4 mm). The obtained granules (320.9 g) were mixed with talc (Matsumurasangyo Co., Ltd., 0.086 g) and light anhydrous silicic acid (NIPPON AEROSIL, 0.086 g) to give granules having the following composition per 750 mg.

TABLE 5

| anhydrous citric acid crystal | 300 mg |
|---|---|
| compound A | 49.59 mg |
| mannitol | 394.01 mg |
| hydroxypropylcellulose | 6 mg |
| talc | 0.2 mg |
| light anhydrous silicic acid | 0.2 mg |
| total | 750 mg |

Example 1

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Anhydrous citric acid crystal (Wako Pure Chemical Industries, Ltd.) was sieved with a round sieve to give anhydrous citric acid crystal on 30 mesh. The anhydrous citric acid crystal (90 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (330 mg) were filled in No. 2 gelatin capsules (Capsugel) to give capsules having the following composition per capsule.

TABLE 6

| anhydrous citric acid crystal | 180.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 330.0 mg |

Example 2

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Anhydrous citric acid crystal (Wako Pure Chemical Industries, Ltd.) was sieved with a round sieve to give anhydrous citric acid crystal on 30 mesh. The anhydrous citric acid crystal (150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (450 mg) were filled in No. 0 gelatin capsules (Capsugel) to give capsules having the following composition per capsule.

TABLE 7

| anhydrous citric acid crystal | 300.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Example 3

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Anhydrous citric acid crystal (Wako Pure Chemical Industries, Ltd.) was sieved with a round sieve to give anhydrous citric acid crystal on 30 mesh. The anhydrous citric acid crystal (175 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (500 mg) were filled in No. 0 gelatin capsules (Capsugel) to give capsules having the following composition per capsule.

TABLE 8

| anhydrous citric acid crystal | 350.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 500.0 mg |

Example 4

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Tartaric acid crystal (Wako Pure Chemical Industries, Ltd.) was sieved with a round sieve to give tartaric acid crystal on 30 mesh (aperture 0.50 mm). The tartaric acid crystal (150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr to give granules at the range of 16-30 mesh (aperture 0.50-1.00 mm). The granules (450 mg) were filled in No. 0 gelatin capsules (Capsugel) to give capsules having the following composition per capsule.

TABLE 9

| tartaric acid crystal | 300.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Example 5

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Malic acid crystal (Wako Pure Chemical Industries, Ltd.) was sieved with a round sieve to give malic acid crystal on 30 mesh (aperture 0.50 mm). The malic acid crystal (150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 16-30 mesh (aperture 0.50-1.00 mm). The granules (450 mg) were filled in No. 0 gelatin capsules (Capsugel) to give capsules having the following composition per capsule.

TABLE 10

| malic acid crystal | 300.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Example 6

Compound A (24.8 g), sucrose (Osaka-Toka. Co., Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Ascorbic acid crystal (Wako Pure Chemical Industries, Ltd.) was sieved with a round sieve to give ascorbic acid crystal on 32 mesh (aperture 0.50 mm). The ascorbic acid crystal (150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 16-30 mesh (aperture 0.50-1.00 mm). The granules (450 mg) were filled in No. 0 gelatin capsules (Capsugel) to give capsules having the following composition per capsule.

TABLE 11

| ascorbic acid crystal | 300.0 mg |
|---|---|
| compound A | 49.6 mg |
| sucrose | 57.4 mg |
| crystalline cellulose | 16.0 mg |
| L-HPC | 25.0 mg |
| hydroxypropylcellulose | 2.0 mg |
| total | 450.0 mg |

Example 7

Compound A (99.2 g), mannitol (ROQUETTE, 114.8 g), crystalline cellulose (Avicel PH-101, Asahi Kasei Corporation, 32.0 g) and L-HPC (LH-31, Shin-Etsu Chemical Co., Ltd., 50.0 g) were thoroughly mixed to give a dusting powder. Anhydrous citric acid crystal (Wako Pure Chemical Industries, Ltd.) was sieved with a round sieve to give anhydrous citric acid crystal on 30 mesh. The anhydrous citric acid crystal (600 g) was fed into a centrifugal fluidized-bed granulator (CF-260, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (450 mg) were filled in No. 0 hypromellose capsules (Qualicaps Co., Ltd.) to give capsules having the following composition per capsule.

TABLE 12

| anhydrous citric acid crystal | 300.0 mg |
|---|---|
| compound A | 49.6 mg |
| mannitol | 57.4 mg |
| crystalline cellulose | 16.0 mg |
| L-HPC | 25.0 mg |
| hydroxypropylcellulose | 2.0 mg |
| total | 450.0 mg |

Example 8

The granules prepared in Example 7 (granules before being filled in capsules, 800 g) were mixed with magnesium stearate (TAIHEI CHEMICAL INDUSTRIAL CO., LTD., 4.0 g). The obtained CF granules were tableted using a rotary tableting machine (correct K19, KIKUSUI SEISAKUSHO LTD.) mounted with a die and punch (punch: φ10 mm, 8.5R) at a tableting pressure of 2 ton/cm$^2$ to give 452 mg per tablet.

Example 9

The granules prepared in Example 7 (the granules before being filled in capsules, 80 g) were fed into a centrifugal fluidized-bed granulator (CF-mini, Freund Corporation) and coated with carmellose calcium (GOTOKU CHEMICAL COMPANY Ltd., ECG505, 20 g) as a dusting powder while spraying a solution (6 w/v %) of hydroxypropylcellulose (HPC-SL, NIPPON SODA CO., LTD.) in isopropyl alcohol. The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (80 g) were mixed with magnesium stearate (TAIHEI CHEMICAL INDUSTRIAL CO., LTD., 0.4 g). The obtained CF granules (565.3 mg) were weighed and tabletted using a die and punch (punch: φ10 mm, 8.5R) and Auto-graph (AG-IS 50 kN, Shimadzu Corporation) at a tabletting pressure of 2 ton/cm² to give tablets having the following composition per tablet.

TABLE 13

| anhydrous citric acid crystal | 300.0 mg |
|---|---|
| compound A | 49.6 mg |
| mannitol | 57.4 mg |
| crystalline cellulose | 16.0 mg |
| L-HPC | 25.0 mg |
| hydroxypropylcellulose | 2.0 mg |
| croscarmellose calcium | 112.5 mg |
| magnesium stearate | 2.8 mg |
| total | 565.3 mg |

Example 10

The granules prepared in Example 7 (the granules before being filled in capsules, 80 g) were fed into a centrifugal fluidized-bed granulator (CF-mini, Freund Corporation) and coated with croscarmellose sodium (Asahi Kasei Corporation, Ac-Di-Sol, 20 g) as a dusting powder while spraying a solution (6 w/v %) of hydroxypropylcellulose (HPC-SL, NIPPON SODA CO., LTD.) in isopropyl alcohol (Wako Pure Chemical Industries, Ltd.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (80 g) were mixed with magnesium stearate (TAIHEI CHEMICAL INDUSTRIAL CO., LTD., 0.4 g). The obtained CF granules (565.3 mg) were weighed and tabletted using a die and punch (punch: φ10 mm, 8.5R) and Auto-graph (AG-IS 50 kN, Shimadzu Corporation) at a tabletting pressure of 2 ton/cm² to give tablets having the following composition per tablet.

TABLE 14

| anhydrous citric acid crystal | 300.0 mg |
|---|---|
| compound A | 49.6 mg |
| mannitol | 57.4 mg |
| crystalline cellulose | 16.0 mg |
| L-HPC | 25.0 mg |
| hydroxypropylcellulose | 2.0 mg |
| croscarmellose sodium | 112.5 mg |
| magnesium stearate | 2.8 mg |
| total | 565.3 mg |

Example 11

The granules prepared in Example 7 (the granules before being filled in capsules, 80 g) were fed into a centrifugal fluidized-bed granulator (CF-mini, Freund Corporation) and coated with crospovidone (Kollidon CL-M, BASF JAPAN LTD., 20 g) as a dusting powder while spraying a solution (6 w/v %) of hydroxypropylcellulose (HPC-SL, NIPPON SODA CO., LTD.) in isopropyl alcohol (Wako Pure Chemical Industries, Ltd.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 14-30 mesh (aperture 0.50-1.18 mm). The granules (80 g) were mixed with magnesium stearate (TAIHEI CHEMICAL INDUSTRIAL CO., LTD., 0.4 g). The obtained CF granules (565.3 mg) were weighed and tabletted using a die and punch (punch: ϕ10 mm, 8.5R) and Auto-graph (AG-IS 50 kN, Shimadzu Corporation) at a tabletting pressure of 2 ton/cm² to give tablets having the following composition per tablet.

TABLE 15

| anhydrous citric acid crystal | 300.0 mg |
|---|---|
| compound A | 49.6 mg |
| mannitol | 57.4 mg |
| crystalline cellulose | 16.0 mg |
| L-HPC | 25.0 mg |
| hydroxypropylcellulose | 2.0 mg |
| crospovidone | 112.5 mg |
| magnesium stearate | 2.8 mg |
| total | 565.3 mg |

Example 12

Compound A (24.8 g), trehalose dihydrate (Wako Pure Chemical Industries, Ltd., 28.7 g), crystalline cellulose (Avicel PH-101, Asahi Kasei Corporation, 8.0 g) and L-HPC (LH-31, Shin-Etsu Chemical Co., Ltd., 12.5 g) were thoroughly mixed to give a dusting powder. Anhydrous citric acid crystal (Wako Pure Chemical Industries, Ltd.) was sieved with a round sieve to give anhydrous citric acid crystal of 30 mesh or above. The anhydrous citric acid crystal (150 g) was fed into a centrifugal fluidized-bed granulator (CF-mini, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a constant temperature vacuum drying oven (DP43, YAMATO SCIENTIFIC CO., LTD.) at 40° C. for 16 hr, and sieved with a round sieve to give granules at the range of 16-30 mesh (aperture 0.50-1.00 mm). The granules (450 mg) were filled in gelatin capsules No. 0 (Capsugel) to give capsules having the following composition per capsule.

TABLE 16

| anhydrous citric acid crystal | 300.0 mg |
|---|---|
| compound A | 49.6 mg |
| trehalose | 57.4 mg |
| crystalline cellulose | 16.0 mg |
| L-HPC | 25.0 mg |
| hydroxypropylcellulose | 2.0 mg |
| total | 450.0 mg |

Example 13

Compound A (228.1 g), mannitol (ROQUETTE, 267.8 g), crystalline cellulose (Avicel PH-101, Asahi Kasei Corporation, 59.80 g) and L-HPC (LH-31, Shin-Etsu Chemical Co., Ltd., 115.0 g) were thoroughly mixed to give a dusting powder. The anhydrous citric acid crystal (Jungbunzlauer, 1380 g)

was fed into a centrifugal fluidized-bed granulator (CF-360, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a box vacuum dryer (Kusunoki Machinery Co., Ltd.) at 40° C. for 16 hr, and sieved with a round sieve to give granules at the range of 16-30 mesh (aperture 0.50-1.00 mm). The granules (1791 g) were mixed with talc (Matsumurasangyo Co., Ltd., 4.4 g) and light anhydrous silicic acid (AEROSIL, NIPPON AEROSIL, 4.4 g). The obtained granules (450 mg) were filled in No. 0 hypromellose capsules (Qualicaps Co., Ltd.) to give capsules having the following composition per capsule.

TABLE 17

| anhydrous citric acid crystal | 300.0 mg |
| compound A | 49.6 mg |
| mannitol | 58.2 mg |
| crystalline cellulose | 13.0 mg |
| L-HPC | 25.0 mg |
| hydroxypropylcellulose | 2.0 mg |
| talc | 1.1 mg |
| light anhydrous silicic acid | 1.1 mg |
| total | 450.0 mg |

Example 14

Compound A (228.1 g), mannitol (ROQUETTE, 327.6 g) and L-HPC (LH-32, Shin-Etsu Chemical Co., Ltd., 115.0 g) were thoroughly mixed to give a dusting powder. Anhydrous citric acid crystal (Jungbunzlauer, 1380 g) was fed into a centrifugal fluidized-bed granulator (CF-360, Freund Corporation) and coated with the above-mentioned dusting powder while spraying an aqueous solution (4 w/v %) of hydroxypropylcellulose (HPC-SL, NIPPON SODA CO., LTD.). The obtained spherical granules were dried under reduced pressure to at 40° C. for 16 hr, and sieved with a round sieve to give granules at the range of 16-30 mesh (aperture 0.50-1.00 mm). The granules (1791 g) were mixed with talc (Matsumurasangyo Co., Ltd., 4.4 g) and light anhydrous silicic acid (AEROSIL, NIPPON AEROSIL, 4.4 g). The obtained granules (450 mg) were filled in No. 0 hypromellose capsules (Qualicaps Co., Ltd.) to give capsules having the following composition per capsule.

TABLE 18

| anhydrous citric acid crystal | 300.0 mg |
| compound A | 49.6 mg |
| mannitol | 71.2 mg |
| L-HPC | 25.0 mg |
| hydroxypropylcellulose | 2.0 mg |
| talc | 1.1 mg |
| light anhydrous silicic acid | 1.1 mg |
| total | 450.0 mg |

Example 15

Compound A (239.5 g), mannitol (ROQUETTE, 343.9 g), L-HPC (LH-32, Shin-Etsu Chemical Co., Ltd., 120.8 g) and hydroxypropylcellulose (HPC-SL, NIPPON SODA CO., LTD., 9.660 g) were thoroughly mixed to give a dusting powder. Anhydrous citric acid crystal (Jungbunzlauer, 1380 g) was fed into a centrifugal fluidized-bed granulator (CF-360, Freund Corporation) and coated with the above-mentioned dusting powder while spraying purified water. The obtained spherical granules were dried under reduced pressure in a box vacuum dryer (Kusunoki Machinery Co., Ltd.) at 40° C. for 16 hr, and sieved with a round sieve to give granules at the range of 16-30 mesh (aperture 0.50-1.00 mm). The granules (1791 g) were mixed with talc (Matsumurasangyo Co., Ltd., 4.4 g) and light anhydrous silicic acid (AEROSIL, NIPPON AEROSIL, 4.4 g). The obtained granules (450 mg) were filled in No. 0% hypromellose capsules (Qualicaps Co., Ltd.) to give capsules having the following composition per capsule.

TABLE 19

| anhydrous citric acid crystal | 300.0 mg |
| compound A | 49.6 mg |
| mannitol | 71.2 mg |
| L-HPC | 25.0 mg |
| hydroxypropylcellulose | 2.0 mg |
| talc | 1.1 mg |
| light anhydrous silicic acid | 1.1 mg |
| total | 450.0 mg |

Example 16

Compound A (239.5 g), mannitol (ROQUETTE, 343.9 g), L-HPC (LH-32, Shin-Etsu Chemical Co., Ltd., 120.8 g) and hydroxypropylcellulose (HPC-L, NIPPON SODA CO., LTD., 9.660 g) were thoroughly mixed to give a dusting powder. Anhydrous citric acid crystal (Jungbunzlauer, 1380 g) was fed into a centrifugal fluidized-bed granulator (CF-360, Freund Corporation) and coated with the above-mentioned dusting powder while spraying purified water. The obtained spherical granules were dried under reduced pressure in a box vacuum dryer (Kusunoki Machinery Co., Ltd.) at 40° C. for 16 hr, and sieved with a round sieve to give granules at the range of 16-30 mesh (aperture 0.50-1.00 mm). The granules (1791 g) were mixed with talc (Matsumurasangyo Co., Ltd., 4.4 g) and light anhydrous silicic acid (AEROSIL, NIPPON AEROSIL, 4.4 g). The obtained granules (450 mg) were filled in No. 0 hypromellose capsules (Qualicaps Co., Ltd.) to give capsules having the following composition per capsule.

TABLE 20

| anhydrous citric acid crystal | 300.0 mg |
| compound A | 49.6 mg |
| mannitol | 71.2 mg |
| L-HPC | 25.0 mg |
| hydroxypropylcellulose | 2.0 mg |
| talc | 1.1 mg |
| light anhydrous silicic acid | 1.1 mg |
| total | 450.0 mg |

Example 17

Compound A (239.5 g), mannitol (ROQUETTE, 372.9 g) and L-HPC (LH-32, Shin-Etsu Chemical Co., Ltd., 96.6 g) were thoroughly mixed to give a dusting powder. Anhydrous citric acid crystal (Jungbunzlauer, 1610 g) was fed into a centrifugal fluidized-bed granulator (CF-360, Freund Corporation) and coated with the above-mentioned dusting powder while spraying an aqueous solution (2 w/v %) of hydroxypropylcellulose (HPC-SL, NIPPON SODA CO., LTD.). The obtained spherical granules were dried under reduced pressure in a box vacuum dryer (Kusunoki Machinery Co., Ltd.) at 40° C. for 16 hr, and sieved with a round sieve to give granules at the range of 16-30 mesh (aperture 0.50-1.00 mm). The granules (1991 g) were mixed with talc (Matsumurasangyo Co., Ltd., 4.4 g) and light anhydrous silicic acid (AEROSIL, NIPPON AEROSIL, 4.4 g). The obtained granules (500 mg) were filled in No. 0 hypromellose capsules (Qualicaps Co., Ltd.) to give capsules having the following composition per capsule.

TABLE 21

| anhydrous citric acid crystal | 350.0 mg |
| compound A | 49.6 mg |
| mannitol | 77.2 mg |
| L-HPC | 20.0 mg |
| hydroxypropylcellulose | 1.0 mg |
| talc | 1.1 mg |
| light anhydrous silicic acid | 1.1 mg |
| total | 500.0 mg |

Example 18

Compound A (239.5 g), mannitol (ROQUETTE, 315.0 g) and L-HPC (LH-32, Shin-Etsu Chemical Co., Ltd., 144.9 g) were thoroughly mixed to give a dusting powder. Anhydrous citric acid crystal (Jungbunzlauer, 1150 g) was fed into a centrifugal fluidized-bed granulator (CF-360, Freund Corporation) and coated with the above-mentioned dusting powder while spraying an aqueous solution (6 w/v %) of hydroxypropylcellulose (HPC-SL, NIPPON SODA CO., LTD.). The obtained spherical granules were dried under reduced pressure in a box vacuum dryer (Kusunoki Machinery Co., Ltd.) at 40° C. for 16 hr, and sieved with a round sieve to give granules at the range of 16-30 mesh (aperture 0.50-1.00 mm). The granules (1591 g) were mixed with talc (Matsumurasangyo Co., Ltd., 4.4 g) and light anhydrous silicic acid (AEROSIL, NIPPON AEROSIL, 4.4 g). The obtained granules (400 mg) were filled in No. 0 hypromellose capsules (Qualicaps Co., Ltd.) to give capsules having the following composition per capsule.

TABLE 22

| anhydrous citric acid crystal | 250.0 mg |
| compound A | 49.6 mg |
| mannitol | 65.2 mg |
| L-HPC | 30.0 mg |
| hydroxypropylcellulose | 3.0 mg |
| talc | 1.1 mg |
| light anhydrous silicic acid | 1.1 mg |
| total | 400.0 mg |

Example 19

Compound A (228.1 g), mannitol (ROQUETTE, 335.8 g) and L-HPC (LH-32 Shin-Etsu Chemical Co., Ltd., 115.0 g) were mixed to give a dusting powder. Hydroxypropylcellulose (HPC-SSL, NIPPON SODA CO., LTD., 9.2 g) was dissolved in purified water (194.6 g) to give a binding liquid. Anhydrous citric acid crystal (Jungbunzlauer, 1380 g) was fed into a centrifugal fluidized-bed granulator (CF-360, Freund Corporation) and coated with the dusting powder while spraying the binding liquid. The obtained granules were dried under reduced pressure at 40° C. for 18 hr, and sieves of 16 mesh and 42 mesh were used to give granules at the range of 16-42 mesh (aperture 0.355-1.00 mm). The granules (7193.6 g) were mixed with talc (Matsumurasangyo Co., Ltd., 3.2 g) and light anhydrous silicic acid (AEROSIL, NIPPON AEROSIL, 3.2 g) in a tumbler mixer (60 L, Showa Kagaku Kikai Kosakusho Co., Ltd.) to give pioglitazone hydrochloride granules having the following composition per 450 mg.

TABLE 23

| anhydrous citric acid crystal | 300 mg |
| compound A | 49.59 mg |
| mannitol | 73.01 mg |
| L-HPC | 25 mg |
| hydroxypropylcellulose | 2 mg |
| talc | 0.2 mg |
| light anhydrous silicic acid | 0.2 mg |
| total | 450 mg |

Example 20

The pioglitazone hydrochloride granules obtained in Example 19 (150 mg) are filled in No. 4 hypromellose capsules (Qualicaps Co., Ltd.) using a capsule filling machine (Zanasi 6F, IMA) to give capsules having the following composition.

TABLE 24

| component | amount added |
|---|---|
| pioglitazone hydrochloride granule | 150 mg |
| No. 4 hypromellose capsule | 1 capsule |

Example 21

The pioglitazone hydrochloride granules obtained in Example 19 (300 mg) are filled in No. 1 hypromellose capsules (Qualicaps Co., Ltd.) using a capsule filling machine (Zanasi 6F, IMA) to give capsules having the following composition.

TABLE 25

| component | amount added |
|---|---|
| pioglitazone hydrochloride granule | 300 mg |
| No. 1 hypromellose capsule | 1 capsule |

Example 22

The pioglitazone hydrochloride granules obtained in Example 19 (450 mg) were filled in No. 0 hypromellose capsules (Qualicaps Co., Ltd.) using a capsule filling machine (Zanasi 6F, IMA) to give capsules having the following composition.

TABLE 26

| component | amount added |
|---|---|
| pioglitazone hydrochloride granule | 450 mg |
| No. 0 hypromellose capsule | 1 capsule |

Example 23

Compound A (24.8 g), mannitol (ROQUETTE, 159.5 g) and L-HPC (LH-32, Shin-Etsu Chemical Co., Ltd., 37.5 g) were thoroughly mixed to give a dusting powder. Anhydrous citric acid crystal (Jungbunzlauer, 150 g) was fed into a centrifugal fluidized-bed granulator (CF-mini, Freund Corporation) and coated with the above-mentioned dusting powder while spraying an aqueous solution (3 w/v %) of hydroxypropylcellulose (HPC-SL, NIPPON SODA CO., LTD.). The obtained spherical granules were dried under reduced pressure at 40° C. for 16 hr, and sieved with a round sieve to give granules at the range of 12-30 mesh (aperture 0.50-1.4 mm). The granules (244.7 g) were mixed with talc (Matsumurasangyo Co., Ltd., 0.065 g) and light anhydrous silicic acid (NIPPON AEROSIL, 0.065 g) to give granules having the following composition per 750 mg.

TABLE 27

| | |
|---|---|
| anhydrous citric acid crystal | 300 mg |
| compound A | 49.59 mg |
| mannitol | 319.01 mg |
| L-HPC | 75 mg |
| hydroxypropylcellulose | 6 mg |
| talc | 0.2 mg |
| light anhydrous silicic acid | 0.2 mg |
| total | 750 mg |

Reference Example 1

A mixture of compound A (80 parts) and crystalline cellulose (CEOLUS PH-101, Asahi Kasei Corporation, 20 parts) was pulverized in a jet mill (PJM-100SP, NIPPON PNEUMATIC MFG. CO., LTD.) to give a ground product C.

A mixture of the ground product C (70 g), metformin hydrochloride (847.1 g) and crystalline cellulose (25.1 g) was subjected to fluidized-bed granulation (POWREX CORPORATION, MP-10) while spraying an aqueous solution (261 g) of povidone (29.1 g), and passed through a power mill to give milled granule A. The obtained milled granule A (856 g) was mixed with crystalline cellulose (57.3 g), croscarmellose sodium (45.5 g) and magnesium stearate (3.0 g) to give a powder mixture. The thus-obtained powder mixture was tableted using a rotary tableting machine (KIKUSUI SEISAKUSHO LTD., Purepress correct 12HUK) at a tableting pressure of about 10 kN/punch (14×9 mm oblong) to give tablets containing pioglitazone hydrochloride (33.1 mg) and metformin hydrochloride (500 mg) per tablet (weight of one tablet 663 mg).

Reference Example 2

A mixture of the ground product C (304.4 g) obtained in Reference Example 1, metformin hydrochloride (3596.2 g) and crystalline cellulose (95.6 g) was subjected to fluidized-bed granulation (POWREX CORPORATION, FD-5S) while spraying an aqueous solution (1240 g) of povidone (252 g), and passed through a power mill to give milled granule A. The obtained milled granule A (6844 g) was mixed with crystalline cellulose (458.2 g), croscarmellose sodium (365.4 g) and magnesium stearate (23.2 g) to give a powder mixture. The thus-obtained powder mixture was tableted using a rotary tableting machine (KIKUSUI SEISAKUSHO LTD., AQUA08242L2J1) at a tableting pressure of about 17 kN/punch (14×9 mm oblong) to give tablets containing pioglitazone hydrochloride (33.1 mg) and metformin hydrochloride (500 mg) per tablet (weight of one tablet 663 mg).

The obtained tablets (3978 g) were fed into a coating apparatus (POWREX CORPORATION, DRIACOATER DRC-500), film coated by spraying at an air supply temperature 90° C., 14-21 g/min to give film-coated tablets weighing 683 mg per tablet. The coating solution (1568 g) used was obtained by dispersing or dissolving hypromellose (162 g), macrogol 6000 (32.5 g), talc (32.5 g), titanium oxide (32.5 g) and yellow ferric oxide (0.52 g) in purified water (2340 g).

Reference Example 3

The milled granule A (118.0 g) obtained in Reference Example 2 was mixed with crystalline cellulose (7.9 g), carmellose calcium (6.3 g) and magnesium stearate (0.4 g) to give a powder mixture. The thus-obtained powder mixture was tableted using an Auto-graph (Shimadzu Corporation, AG-50 kN) at a tableting pressure of about 14.5 kN/punch (14×9 mm oblong) to give tablets containing pioglitazone hydrochloride (33.1 mg) and metformin hydrochloride (500 mg) per tablet (weight of one tablet 663 mg).

Experimental Example 1

ACTOS tablet (45 mg) (trade name) and the capsules of Comparative Example 1 and Example 3 were subjected to a dissolution test according to the Paddle Method (50 rpm) and using McIlvaine buffer adjusted to pH 3.0 as a test solution. The eluate was filtered using a 0.45 μm filter, and the eluted compound A was measured by high performance liquid chromatography (Hitachi, Ltd.).

As a result, the elution rate of compound A from the ACTOS tablet and the capsules of Comparative Example 1 and Example 3 after 15 minutes was 22.8%, 61.7% and 98.5%, respectively.

It was clarified that citric acid improves the elution rate of compound A, and that, of the capsules of Comparative Example 1 and Example 3 containing almost the same amount of citric acid, the capsule of Example 3 shows remarkably high elution rate.

Experimental Example 2

The ACTOS tablet (45 mg) (trade name) and the capsules of Comparative Examples 1-3 and Examples 2-5 were administered at a dose of 45 mg (amount corresponding to pioglitazone) to beagles fasted from the previous day. After the administration, plasma concentration was measured at 30 min, 1 hr, 2 hr, 3 hr, 4 hr and 8 hr later, and plasma area under the curve [AUC (μg·h/mL)] was calculated by the trapezoid formula. Moreover, the relative standard deviation (RSD) of AUC was calculated as an index of variation of interindividual absorption, and AUC increase rate (%) relative to the ACTOS tablet was calculated as an index of absorption-promoting effect. In addition, the bioavailability was calculated by the following formula:

Bioavailability(%)=(AUC of oral administration/AUC of intravenous administration)×100

The results are shown below. In the Table, AUC shows mean±SD and "solution" means 0.5M solution of pioglitazone hydrochloride in citric acid.

TABLE 28

| preparation | AUC (mg/h/mL) | RSD (%) | absorption-promoting effect (%) | bioavailability |
|---|---|---|---|---|
| solution | 10.927 ± 2.228 | 20.4 | — | 94 |
| ACTOS tablet | 5.497 ± 2.587 | 47.1 | 0 | 47 |
| Comparative Example 1 | 8.403 ± 2.572 | 30.6 | +53 | 72 |
| Comparative Example 2 | 3.818 ± 2.073 | 54.3 | −31 | 33 |
| Comparative Example 3 | 3.476 ± 1.142 | 32.9 | −37 | 30 |
| Example 2 | 11.496 ± 2.283 | 19.9 | +109 | 99 |
| Example 3 | 11.826 ± 1.419 | 12.0 | +115 | 102 |
| Example 4 | 13.085 ± 1.324 | 10.1 | +138 | 113 |
| Example 5 | 10.648 ± 1.054 | 9.9 | +94 | 92 |

As is clear from the Table, the ACTOS tablet and the capsule of Comparative Example 2 free of an organic acid showed low AUC and high RSD. A comparison of the capsules of Comparative Example 1 and Example 3 containing almost the same amount of citric acid revealed a remarkably higher absorption-promoting effect and smaller RSD of the capsule of Example 3.

In addition, the capsules of Examples 2, 4 and 5 containing citric acid, tartaric acid and malic acid, respectively, showed about 2-fold absorption-promoting effect and RSD was also improved. In contrast, the capsule of Comparative Example 3 containing fumaric acid did not show an absorption-promoting effect and high RSD.

The capsules of Examples 2-5 showed higher bioavailability as compared to the capsules of Comparative Examples 1-3.

Experimental Example 3

The granules (before filling in capsules) obtained in Comparative Examples 2 and 3, and Examples 2-6 were subjected to a dissolution test according to the Paddle Method (50 rpm) and using McIlvaine buffer adjusted to pH 3.0 as a test solution. The eluate was filtered using a 0.45 μm filter, and the eluted compound A was measured by HPLC (Hitachi, Ltd.).

As a result, the elution rate of compound A from the granules of Comparative Examples 2 and 3, and Examples 2, 4, 5 and 6 after 15 minutes was 34.3%, 32.4%, 105.2%, 95.5%, 96.9% and 57.7%, respectively.

It was clarified that citric acid, tartaric acid, malic acid and ascorbic acid improve the elution rate of compound A, and that fumaric acid does not improve the elution rate of compound A.

Experimental Example 4

The ACTOS tablet (45 mg) (trade name), the capsule obtained in Example 7 and the tablet obtained in Example 8 were administered at a dose of 45 mg (amount corresponding to pioglitazone) to beagles fasted from the previous day and given an intramuscular injection of pentagastrin (40 μg/kg body weight) 15 minutes before administration and 30 minutes after administration. After the administration, plasma concentration was measured at 30 min, 1 hr, 2 hr, 3 hr, 4 hr and 8 hr later, and plasma area under the curve [AUC (μg.h/mL)] was calculated by the trapezoid formula. Moreover, the relative standard deviation (RSD) of AUC was calculated as an index of variation of interindividual absorption, and AUC increase rate (%) relative to the ACTOS tablet was calculated as an index of absorption-promoting effect. In addition, the maximum blood concentration [Cmax (μg/mL)] was also measured. The results are shown below. In the Table, AUC shows mean±SD.

TABLE 29

| preparation | AUC (μg h/mL) | RSD (%) | absorption-promoting effect (%) | Cmax (μg/mL) |
|---|---|---|---|---|
| ACTOS tablet | 10.186 ± 5.299 | 52.0 | 0 | 3.050 ± 1.708 |
| Example 7 | 15.791 ± 2.089 | 13.2 | +55 | 5.271 ± 0.728 |
| Example 8 | 18.627 ± 1.165 | 6.3 | +83 | 6.451 ± 1.269 |

As is clear from the Table, the capsule of Example 7 and the tablet of Example 8, containing citric acid, showed a remarkable absorption-promoting effect and remarkably improved RSD in beagles having a decreased gastric pH by a pentagastrin treatment, as compared to the ACTOS tablet.

In addition, the capsule of Example 7 and the tablet of Example 8 increased the maximum blood concentration as compared to the ACTOS tablet.

Experimental Example 5

The granules obtained in Examples 2, 7 and 12 (before filling in capsule) were placed in 3 glass bottles for each Example, a first one was tightly sealed, a second one with an open cap was sealed in a 33% RH atmosphere desiccator, and a third one with an open cap was sealed in a 44% RH atmosphere desiccator. They were preserved for 2 months in a constant-temperature device at 40° C. The whiteness of the granules in the glass bottles was visually confirmed before and after the preservation.

As a result, the granule obtained in Example 2 turned yellow-brown under any preservation conditions, whereas the granules obtained in Example 7 and Example 12 remained white with no color change. Thus, a suppressive effect on preparation color change due to mannitol and trehalose could be confirmed.

Experimental Example 6

Actos tablet (45 mg) (trade name) and the capsule of Example 22 were subjected to a dissolution test according to the Paddle Method (50 rpm) and using KCl-HCl buffer (pH 2.0), McIlvaine buffer (pH 2.2), McIlvaine buffer (pH 2.5) and McIlvaine buffer (pH 3.0) as test solutions. The eluate was filtered using a 0.45 μm filter at 15 minutes from the start of the test, and the eluted compound A was measured by high performance liquid chromatography (Shimadzu Corporation).

As a result, the elution rate of compound A from the ACTOS tablet after 15 minutes was 95% at pH 2.0, 78% at pH2.2, 53% at pH 2.5 and 39% at pH 3.0, and 87% at pH 2.0, 102% at pH 2.2, 97% at pH 2.5 and 104% at pH 3.0 for Example 22. The capsule of Example 22 showed faster elution rates and higher eluted amounts at pH 2.2, 2.5 and 3.0, as compared to ACTOS tablet.

The results confirm that the capsule of the present invention is not easily affected by pH change as compared to ACTOS tablet, and shows improved solubility of pioglitazone.

Experimental Example 7

Figure 1B:
Figure 2A:
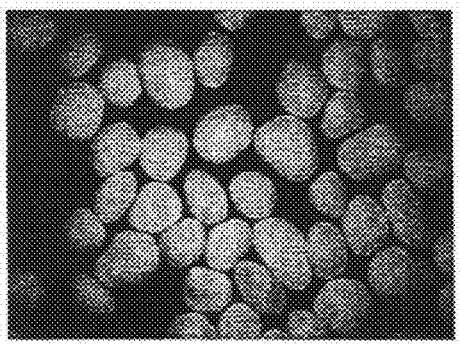
FIG. 2A is a photograph showing the state of granules before the dissolution test.
Figure 2B:
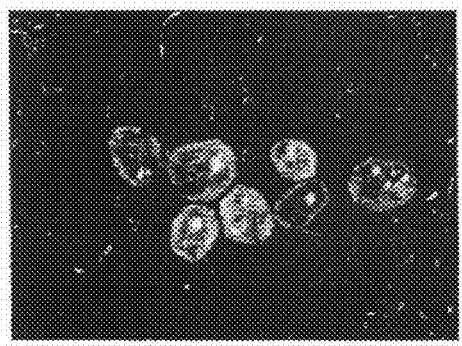
FIG. 2B shows the granules at 5 min after the start of the test.
Figure 2C:
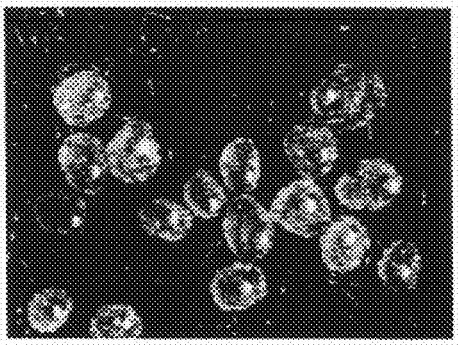
FIG. 2C shows the granules at 10 min after the start of the test.
Figure 2D:
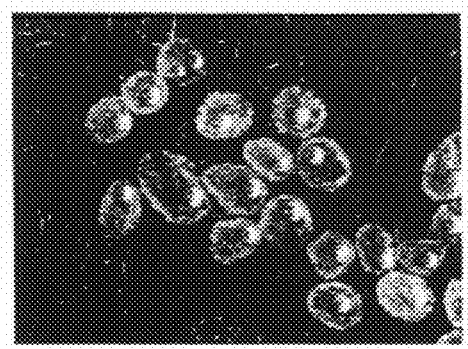
FIG. 2D shows the granules at 60 min after the start of the test.

The pioglitazone hydrochloride granule obtained in Example 19 was subjected to a dissolution test according to the Paddle Method (50 rpm) and using McIlvaine buffer (900 mL, pH 3.0) as a test solution. The state of the granule before the dissolution test, and 5, 10 and 60 minutes after the start of the dissolution test was observed with a microscope. The photographs showing the state of granule is shown in FIG. 1 (A and B) and FIG. 2 (A-D). As a result, pioglitazone hydrochloride was almost dissolved in 5 minutes after the start of the test, and 100% dissolved in 10 minutes after the start of the test. However, the construct having, as a skeleton, a cellulose derivative constituting a coating layer was maintained even at 60 minutes after the start of the test (FIG. 2D). Water and air were observed in the membrane of the to construct after elution (FIG. 1B).

Experimental Example 8

The granules obtained in Comparative Example 4, Comparative Example 5 and Example 23 were subjected to a dissolution test according to the Paddle Method (50 rpm) and using McIlvaine buffer (pH 3.0, 900 mL) as a test solution. The eluate was filtered using a 0.45 μm filter at 5 minutes from the start of the test, and the eluted compound A was measured using a UV visible spectrophotometer.

As a result, the elution rate in 5 minutes of compound A from the granules of Comparative Example 4, Comparative Example 5 and Example 23 was 63.3%, 90.7% and 98.6%, respectively.

The results have clarified that, even though all granules contain equivalent amounts of anhydrous citric acid crystal and compound A, the granule of the present invention containing low-substituted hydroxypropylcellulose in a coating layer shows a high elution rate as compared to the granule free of low-substituted hydroxypropylcellulose in a coating layer.

INDUSTRIAL APPLICABILITY

The coated preparation of the present invention is a superior preparation, since it shows high bioavailability of pioglitazone, a sufficient effect with a low dose, and less interindividual variation in blood drug concentration.

In addition, the coated preparation of the present invention containing mannitol or trehalose in a coating layer is a superior preparation, since it shows high bioavailability of pioglitazone, less interindividual variation in blood drug concentration, and suppressed color change (particularly color change under preservation conditions).

This application is based on a patent application No. 2007-183749 filed in Japan, the contents of which are incorporated in full herein by this reference.

The invention claimed is:

1. A preparation comprising
a core comprising a pharmaceutically acceptable organic acid with water solubility at 20° C. of not less than 10 mg/mL and a negative common logarithm $pK_{a1}$ of the first acid dissociation constant $K_{a1}$ at 25° C. of not more than 5, and
a coating layer comprising pioglitazone hydrochloride, and further comprising (1) mannitol or trehalose, and (2) low-substituted hydroxypropylcellulose,
wherein the pharmaceutically acceptable organic acid is selected from a group consisting of citric acid, tartaric acid, malic acid and ascorbic acid,
wherein the weight ratio of pioglitazone to the pharmaceutically acceptable organic acid is 1:4 to 1:26, and
wherein the content of the pharmaceutically acceptable organic acid contained in the core is 20-95 parts by weight, per 100 parts by weight of the preparation, and
wherein the content of the low-substituted hydroxypropylcellulose in the coating layer is 0.5-70 parts by weight, per 100 parts by weight of the coating layer.

2. The preparation of claim 1, wherein the pharmaceutically acceptable organic acid is citric acid.

3. The preparation of claim 1, wherein the pharmaceutically acceptable organic acid is citric acid crystal.

4. The preparation of claim 1, which shows bioavailability exceeding 75% in a dog.

5. The preparation of claim 1, wherein the pharmaceutically acceptable organic acid is at least one kind of crystals selected from citric acid, tartaric acid, malic acid and ascorbic acid.

6. The preparation of claim 1, wherein the core consists of the pharmaceutically acceptable organic acid.

7. The preparation of claim 1, wherein pioglitazone hydrochloride is a sole active ingredient.

* * * * *